United States Patent [19]

Sjogren et al.

[11] Patent Number: 5,034,410
[45] Date of Patent: Jul. 23, 1991

[54] ANTHELMINTICALLY ACTIVE BENZENEPROPANAMIDE DERIVATIVES

[75] Inventors: Eric B. Sjogren, Palo Alto; Michael A. Rider, Hayward, both of Calif.

[73] Assignee: Syntex (U.S.A.) Inc., Palo Alto, Calif.

[21] Appl. No.: 420,076

[22] Filed: Oct. 11, 1989

[51] Int. Cl.$^5$ ............ C07C 255/33; A01N 37/34
[52] U.S. Cl. .................. 514/516; 514/521; 514/522; 558/11; 558/13; 558/392
[58] Field of Search ......... 514/521, 516, 522; 558/392, 11, 13

[56] References Cited

U.S. PATENT DOCUMENTS

| | | | |
|---|---|---|---|
| 4,061,767 | 12/1977 | Ertel et al. ............ | 424/282 |
| 4,154,849 | 5/1979 | Walker et al. .......... | 514/516 |
| 4,900,349 | 2/1990 | Heaney et al. ......... | 514/521 X |

FOREIGN PATENT DOCUMENTS

| | | |
|---|---|---|
| 2555789 | 7/1977 | Fed. Rep. of Germany . |
| 138772 | 11/1979 | German Democratic Rep. . |
| 139127 | 12/1979 | German Democratic Rep. . |
| 227319 | 9/1978 | U.S.S.R. . |

OTHER PUBLICATIONS

Shoukry, M. M. et al., *Annali Di Chimica*, (1979), vol. 69, No. 5–6, pp. 211–217.
Shoukry, M. M. et al., *Annali Di Chimica*, (1980), vol. 70, No. 5–6, pp. 319–321.
Shoukry, M. M., *Indian Journal of Chemistry* (1984), vol. 23A, No. 6, pp. 537–538.
Barnikow, G., *J. Prakt. Chem.*, (1966), vol. 32, No. 5–6, pp. 259–264.
Dubenko, R. G. et al., *Fiziol. Akt. Veshchestva*, (1978), vol. 10, pp. 99–101.
Dubenko, R. G. et al., *Zh. Org. Khim.*, (1969), vol. 5, No. 3, pp. 529–533.
Dubenko, R. G. et al., *Zh. Org. Khim.*, (1970), vol. 6, No. 8, pp. 1749–1750.
Dubenko, R. G. et al., *Ukr. Khim. Zh.* (1969), vol. 35, No. 8, pp. 886–887.
Rudorf, W. D., *Tetrahedron*, (1978), vol. 34, No. 6, pp. 725–730.
Dubenko, R. G. et al., *Khim. Geterotsikl. Soedin*, (1974), vol. 4, pp. 500–502.
Rudorf, W. D. et al., *J. Prakt. Chem.*, (1978), vol. 320, No. 4, pp. 585–599.
Dehne, H. et al., *J. Prakt. Chem.*, (1980), vol. 322, No. 3, pp. 407–410.
Neplyuev, V. M. et al., *Zh. Org. Khim*, 1974, vol. 10, No. 4, pp. 765–769.

*Primary Examiner*—Joseph Paul Brust
*Attorney, Agent, or Firm*—Carol J. Roth; Derek P. Freyberg; Tom M. Moran

[57] ABSTRACT

This invention is directed to a method for treating helminthiasis in an animal which method comprises administering to an animal in need thereof an anthelmintically effective amount of a compound of the Formula (I):

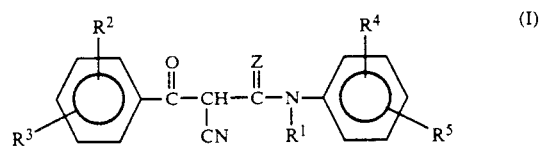

wherein
Z is oxygen or sulfur;
$R^1$ is hydrogen or lower alkyl; and
$R^2$, $R^3$, $R^4$ and $R^5$ are independently hydrogen, halo, lower haloalkyl, lower alkoxy, lower haloalkoxy, nitro, cyano, halophenoxy, haloalkylphenoxy, thiocyano or isothiocyano, provided that $R^2$ and $R^3$ cannot simultaneously be hydrogen and that $R^4$ and $R^5$ cannot simultaneously be hydrogen; or a pharmaceutically acceptable salt thereof, and pharmaceutical compositions formulated therewith. This invention is also directed to novel anthelmintically active benzenepropanamides of Formula (I) wherein Z is oxygen.

31 Claims, No Drawings

ANTHELMINTICALLY ACTIVE BENZENEPROPANAMIDE DERIVATIVES

BACKGROUND OF THE INVENTION

1. Field of the Invention

This invention relates to a method for treating helminthiasis in animals by administering certain benzenepropanamide derivatives or pharmaceutically acceptable salts thereof. This invention also relates to veterinary compositions for treating helminthiasis in animals that are comprised of pharmaceutically acceptable excipients and certain benzenepropanamide derivatives or their pharmaceutically acceptable salts. This invention also relates to novel anthelmintically effective benzenepropanamide derivatives and their pharmaceutically acceptable salts.

2. Related Disclosures

German Offenlegungsschrift No. 25 55 789 (Hoechst AG) discloses compounds of the formula:

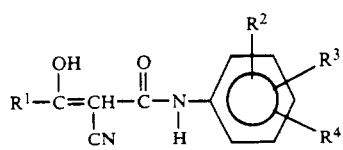

wherein $R^1$ is hydrogen, alkyl or benzyl; $R^2$ is halo, methyl or ethyl optionally substituted by fluoro or chloro, or methyl or ethyl mercaptan; $R^3$ is hydrogen, halo, methyl, ethyl, trifluoromethyl, or methoxy; and $R^4$ is hydrogen, chloro or methoxy; or $R^2$ and $R^3$ together form a —O—CH$_2$—O— group; and their physiologically compatible salts. These compounds are disclosed as having antiinflammatory and analgesic effects. In addition, these compounds are disclosed as having anthelmintic, antimycotic and fungicidal effects.

U.S. Pat. No. 4,061,767 (Hoechst AG) discloses compounds of the formula:

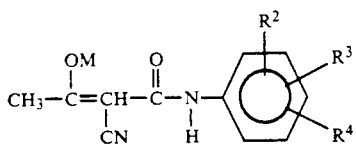

wherein each $R^2$, $R^3$ and $R^4$ is optionally substituted lower alkyl, optionally substituted lower alkoxy, or optionally substituted lower alkylthio, and M is hydrogen, an alkali metal or ammonium. The lower alkyl, lower alkoxy and lower alkylthio substituents may be substituted with halo, nitro, cyano or alkoxycarbonyl groups. $R^3$ may also be phenoxy optionally substituted by halo, alkyl or alkoxy. These compounds are disclosed as having antiinflammatory and analgesic effects.

Unsubstituted α-cyano-β-oxo-N-phenylbenzenepropanamide is disclosed in several references. See, e.g., *Annali Di Chimica*, 1979, Vol. 69, No. 5-6, pp. 211-17; *Annali Di Chimica*, 1980, Vol. 70, No. 5-6, pp. 319-21; and *Indian Journal of Chemistry*, 1984, Vol. 23A, No. 6, pp. 537-8. However, none of these references disclose that this compound is useful in treating helminthiasis in animals.

N-phenylbenzenepropanethioamides are disclosed in several references. See, e.g., *J. Prakt. Chem.*, 1966, Vol. 32, No. 5-6, pp. 259-64; *Fiziol. Akt. Veshchestva*, 1978, Vol. 10, pp. 99-101; *Zh. Org. Khim.*, 1969, Vol. 5, No. 3, pp. 529-33; *Zh. Org. Khim.*, 1970, Vol. 6, No. 8, pp. 1749-50; *Ukr. Khim. Zh.*, 1969, Vol. 35, No. 8, pp. 886-7; *Tetrahedron*, 1978, Vol. 34, No. 6, pp. 725-30; *Khim. Geterotsikl. Soedin.*, 1974, Vol. 4, pp. 500-2; *J. Prakt. Chem.*, 1978, Vol. 320, No. 4, pp. 585-99; *J. Prakt. Chem.*, 1980, Vol. 322, No. 3, pp. 407-10; and *Zh. Org. Khim.*, 1974, Vol. 10, No. 4, pp. 765-9. However, none of these references disclose that N-phenylbenzenepropanethioamides are useful in treating helminthiasis in animals.

In addition, several foreign patents disclose N-phenylbenzenepropanethioamidess. See, e.g., Soviet Union Patent No. 227,319 (Dubenko); and German Democratic Republic Patent Nos. 138,772 and 139,127 (Dehne). However, none of these patents disclose that N-phenylbenzenepropanethioamides are useful in treating helminthiasis in animals.

The disclosures of these and all other documents referred to in this specification are incorporated herein by reference.

SUMMARY OF THE INVENTION

We have discovered that the group of benzenepropanamide derivatives of Formula (I), as shown below:

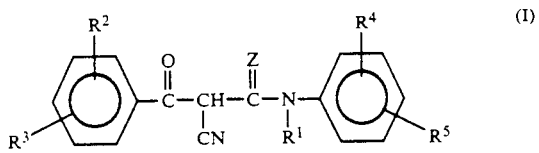

are effective against helminth infestation in animals, and particularly effective against nematode infestation in animals. Accordingly, the invention described and claimed herein contains several different aspects.

In a first aspect, this invention provides a method for treating helminthiasis in an animal which method comprises administering to an animal in need thereof an anthelmintically effective amount of a compound of Formula (I);

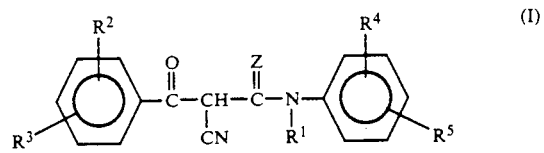

wherein
Z is oxygen or sulfur:
$R^1$ is hydrogen or lower alkyl; and
$R^2$, $R^3$, $R^4$ and $R^5$ are independently hydrogen, halo, lower haloalkyl, lower alkoxy, lower haloalkoxy, nitro, cyano, halophenoxy, haloalkylphenoxy, thiocyano or isothiocyano, provided that $R^2$ and $R^3$ are not simultaneously hydrogen and that $R^4$ and $R^5$ are not simultaneously hydrogen; or a pharmaceutically acceptable salt thereof.

In a second aspect, this invention provides a composition for treating helminthiasis in an animal which composition comprises a pharmaceutically acceptable excipient and an anthelmintically effective amount of a compound of Formula (I) as described above or its pharmaceutically acceptable salt.

In a third aspect, this invention provides novel compounds of Formula (I) wherein Z is oxygen that are useful for treating helminthiasis in animals.

DETAILED DESCRIPTION OF THE INVENTION

Definitions

As used in the specification and appended claims, unless specified to the contrary, the following terms have the meaning indicated:

The term "lower alkyl" refers to a straight or branched chain monovalent radical consisting solely of carbon and hydrogen, containing no unsaturation and having from one to six carbon atoms, i.e., methyl, ethyl, n-propyl, i-propyl, n-butyl, s-butyl, t-butyl, and the like.

The term "lower haloalkyl" refers to a lower alkyl radical as defined above that is substituted by one or more halogen atoms, i.e., trifluoromethyl, difluoromethyl, 2,2,2-trichloroethyl, and the like.

The term "lower alkoxy" refers to a radical of the form —$OR_a$, where $R_a$ is lower alkyl as defined above, i.e., methoxy, ethoxy, n-propoxy, i-propoxy, butoxy, t-butoxy, and the like.

The term "lower haloalkoxy" refers to a lower alkoxy radical as defined above that is substituted by one or more halogen atoms, i.e., trifluoromethoxy, difluoromethoxy, 2,2,2-trichloroethoxy, and the like.

The term "halophenoxy" refers to a phenoxy radical that is substituted by one or more halogen atoms, i.e., 4-chlorophenoxy, 4-bromophenoxy, 2,4-dichlorophenoxy, 2,3,4,5-tetrachlorophenoxy, and the like.

The term "haloalkylphenoxy" refers to a phenoxy radical that is substituted by haloalkyl as defined above, i.e., 4-trifluoromethylphenoxy, 3-trichloromethylphenoxy, 5-(2,2-difluoroethyl)phenoxy, and the like.

The term "pharmaceutically acceptable" as used herein includes that which is acceptable for veterinary use.

The term "pharmaceutically acceptable salt" refers to those salts which retain the biological effectiveness and properties of the free bases and which are not biologically or otherwise undesirable. These salts are prepared from either inorganic or organic bases. Salts derived from inorganic bases include, but are not limited to, the sodium, potassium, lithium, ammonium, calcium, magnesium, ferrous, zinc, copper, manganous, aluminum, ferric, manganic salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally-occuring substituted amines, and cyclic amines, including isopropylamine, trimethylamine, diethylamine, triethylamine, tripropylamine, ethanolamine, 2-dimethylaminoethanol, tromethamine, lysine, arginine, histidine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

The term "animal" includes humans and all domestic and wild mammals and fowl, including, without limitation, cattle, horses, swine, sheep, goats, dogs, cats, rabbits, deer, mink, chickens, ducks, geese, turkeys, game hens, and the like.

The term "treatment" as used herein covers any treatment of a disease in an animal and includes:

(i) preventing the disease from occurring in an animal which may be predisposed to the disease but has not yet been diagnosed as having it;

(ii) inhibiting the disease, i.e., arresting its development; or (iii) relieving the disease, i.e., causing regression of the disease.

The term "anthelmintically effective amount" refers to that amount which, when administered to an animal in need thereof, is sufficient to effect treatment, as defined above, for helminthiasis. Furthermore, an "anthelmintically effective amount" of a compound of Formula (I) for treating helminthiasis will vary depending on the species of helminth, the severity of the infection, and the animal to be treated, but may be determined routinely by one of ordinary skill in the art.

It is understood that the compounds of the present invention exhibit tautomerism. Thus, the compounds of the present invention may exist as the enol tautomer, e.g.,

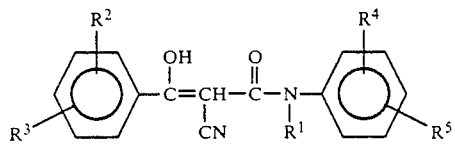

or as the keto tautomer, e.g.,

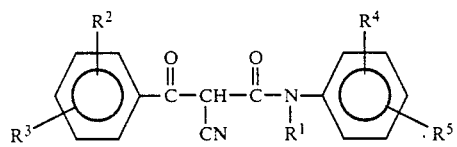

For consistency with established nomenclature for benzenepropanamide derivatives, compounds of the invention are illustrated and named herein as the keto form. However, those skilled in the art will understand that in any particular compound of Formula (I) both tautomers may be present, and the scope of the claims is intended to embrace all such tautomeric forms.

The nomenclature used herein is basically a modified form of I.U.P.A.C. nomenclature wherein compounds of the invention are named as derivatives of benzenepropanamide. The positions in the compounds are indicated as follows:

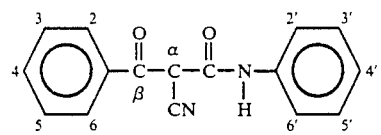

Thus, the following compound is named α-cyano-β-oxo-N-(4'-trifluoromethylphenyl)-(4-trifluoromethyl)-benzenepropanamide:

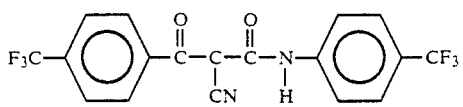

Preferred Embodiments

Within the several aspects of this invention set forth in the Summary of the Invention, certain classes of compounds are preferred. The metes and bounds of these subgroups and their relative degrees of preference are described below.

One aspect of the invention is the group of compounds represented by Formula (I):

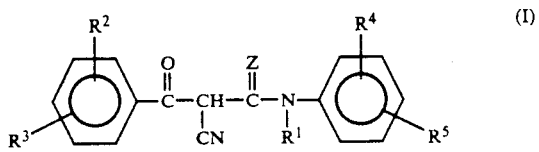

wherein
Z is oxygen;
$R^1$ is hydrogen or lower alkyl; and
$R^2$, $R^3$, $R^4$ and $R^5$ are independently hydrogen, halo, lower haloalkyl, lower alkoxy, lower haloalkoxy, nitro, cyano, halophenoxy, haloalkylphenoxy, thiocyano or isothiocyano, provided that $R^2$ and $R^3$ are not simultaneously hydrogen and that $R^4$ and $R^5$ are not simultaneously hydrogen; or a pharmaceutically acceptable salt thereof.

Within this group of compounds, a preferred class includes those compounds of Formula (I) wherein $R^5$ is in the 4'-position. Preferred $R^5$ substituents within this class are halo, lower haloalkyl, lower haloalkoxy, nitro, cyano, halophenoxy, haloalkylphenoxy or isothiocyano. More preferred $R^5$ substituents within this class are halo, lower haloalkyl or lower haloalkoxy. Most preferred $R^5$ substituent within this class is lower haloalkyl, especially where $R^5$ is trifluoromethyl.

Another preferred class within this group includes those compounds of Formula (I) wherein $R^3$ is in the 4-position. Preferred $R^3$ substituents within this class are halo, lower haloalkyl, lower haloalkoxy, nitro, cyano or halophenoxy. More preferred $R^3$ substituents within this class are halo, lower haloalkyl or lower haloalkoxy. Most preferred $R^3$ substituent in this class is lower haloalkyl, especially where $R^3$ is trifluoromethyl.

Another preferred class within this group includes those compounds wherein $R^3$ is in the 4-position and $R^5$ is in the 4'-position. Preferred $R^3$ and $R^5$ substituents within this class are independently halo, lower haloalkyl, lower haloalkoxy, nitro, cyano, halophenoxy, haloalkylphenoxy or isothiocyano. More preferred $R^3$ and $R^5$ substituents within this class are independently halo, lower haloalkyl, lower haloalkoxy, cyano or nitro. Most preferred $R^3$ and $R^5$ substituent within this class is lower haloalkyl, especially where $R^3$ and $R^5$ are trifluoromethyl.

At the present time, the most preferred compounds of Formula (I) are:
α-cyano-β-oxo-N-(4'-trifluoromethyl)phenyl-(4-trifluoromethyl)benzenepropanamide;
α-cyano-β-oxo-N-(4'-trifluoromethyl)phenyl-(3,5-dichloro)benzenepropanamide;
α-cyano-β-oxo-N-(4'-trifluoromethyl)phenyl-(4-chloro)benzenepropanamide;
α-cyano-β-oxo-N-(3',4'-dichloro)phenyl-(3,4-dichloro)-benzenepropanamide.
α-cyano-β-oxo-N-(4'-chloro)phenyl-(4-chloro)benzenepropanamide;
α-cyano-β-oxo-N-(4'-chloro)phenyl-(3,4-dichloro)benzenepropanamide; and
α-cyano-β-oxo-N-(3',4'-dichloro)phenyl-(4-chloro)benzenepropanamide.

Adminstration and Formulation

An aspect of the present invention relates to pharmaceutical and veterinary compositions useful in the treatment of helmintic infection, comprising an anthelmintically effective amount of a compound of Formula (I), or a pharmaceutically acceptable salt thereof, in admixture with a pharmaceutically acceptable excipient.

Useful pharmaceutical excipients for the preparation of the pharmaceutical compositions hereof can be solids, liquids, gels, creams, ointments, and the like. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "*Remington's Pharmaceutical Sciences*" by E. W. Martin.

In the practice of the above described method of the present invention an anthelmintically effective amount of the compound of Formula (I) or a pharmaceutical composition containing same is administered via any of the usual and acceptable methods known in the art, either singly or in combination with another compound or compounds of the present invention or other pharmaceutical agents. These compounds or compositions can thus be administered orally or intraruminally, systemically (e.g., transdermally, intranasally or by suppository), topically, or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of Formula (I) orally when treating helminth infestations.

In general, an anthelmintically effective amount of a compound of Formula (I) for the treatment of helminthiasis will range from about 1 to about 100 mg per kilogram body weight per day, preferably from about 5 to about 40 mg per kilogram body weight per day. Thus, for administration to an animal weighing 200 kg, the dosage range would be about 200 mg to 20 grams per day.

Synthesis of the Compounds of Formula (I)

A. Synthesis of Compounds of Formula (Ia)

The compounds of Formula (Ia) are compounds of Formula (I) wherein Z is oxygen; $R^1$ is hydrogen or alkyl; $R^2$, $R^3$, $R^4$ and $R^5$ are independently hydrogen, halo, lower haloalkyl, lower alkoxy, lower haloalkoxy, nitro, cyano, halophenoxy, haloalkylphenoxy or thiocyano, provided, however, that $R^2$ and $R^3$ are not simultaneously hydrogen and that $R^4$ and $R^5$ are not simultaneously hydrogen; or the pharmaceutically acceptable salts thereof. The compounds of Formula (Ia) are synthesized from the compounds of Formulae (A) and (C), wherein X is halo, as shown in the following Reaction Scheme 1:

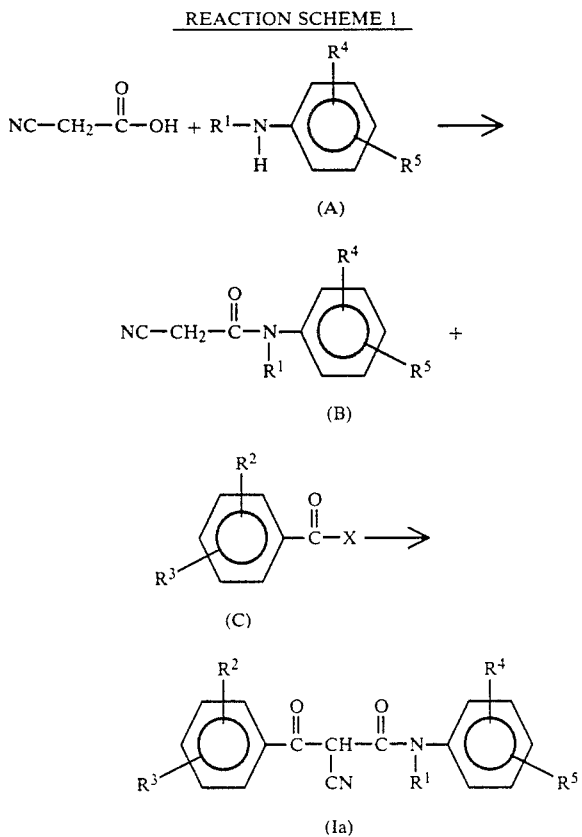

Compounds of Formulae (A) and (C) are commercially available, for example, from Aldrich Chemical Co. Alternatively, they can be prepared by methods known to those skilled in the art. Alternatively, they can be prepared as described in the Preparations below.

In general, the compounds of Formula (Ia) are prepared by first treating a mixture of cyanoacetic acid and an aniline of Formula (A) in an aprotic solvent, for example, dimethylformamide, tetrahydrofuran or dichloromethane, with a condensing agent, for example, dialkyl carbodiimide, preferably diisopropyl carbodiimide, at temperatures from about 0° C. to about 100° C. to form compounds of Formula (B). The reaction is preferably conducted in dimethylformamide at temperatures from about 0° C. to 25° C. for a time sufficient to assure completeness of the reaction, i.e., for about 1 hour to about 24 hours, preferably for about 1 hour to about 3 hours. Resulting compounds of Formula (B) are then dissolved in an aprotic solvent, for example, dimethylformamide, tetrahydrofuran or ethyl ether, preferably tetrahydrofuran, and are then treated with a strong base, e.g., potassium hydride or sodium hydride, preferably sodium hydride. Compounds of Formula (C) in an aprotic solvent, preferably dichloromethane, THF or ether, are then added slowly to the reaction mixture at temperatures at about 0° C. to about 100° C., preferably at about 0° C. to about 25° C., most preferably at about 0° C. to about 10° C., for 1 to 24 hours, preferably for 1 to 3 hours, most preferably for 5 minutes to 1 hour. The reaction mixture is then treated with an acid, preferably hydrochloric acid, to form the compounds of Formula (Ia).

B. Synthesis of Compounds of Formula (Id)

The compounds of Formula (Id) are the compounds of Formula (I) wherein Z is oxygen; $R^1$ is hydrogen; $R^2$, $R^3$ and $R^4$ are independently hydrogen, halo, lower haloalkyl, lower alkoxy, lower haloalkoxy, cyano, halophenoxy or haloalkylphenoxy, provided, however, that $R^2$ and $R^3$ are not simultaneously hydrogen; and $R^5$ is isothiocyano. The compounds of Formula (Id) are synthesized from the compounds of Formula (Ib), as shown in the following Reaction Scheme 2:

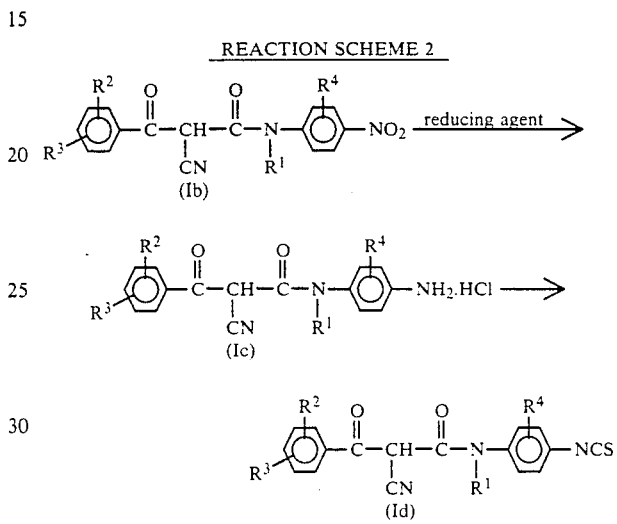

Compounds of Formula (Ib), wherein $R^1$, $R^2$, $R^3$ and $R^4$ are as described for Formula (Id) above, are prepared as described in Reaction Scheme 1 above.

In general, the compounds of Formula (Id) are prepared by first treating compounds of Formula (Ib) in an aqueous acidic solution with a reducing agent, preferably tin(II) chloride dihydrate, at temperatures from about 0° C. to about 100° C., preferably at 80° C. for a time sufficient to assure completeness of the reaction, i.e., for about 1 hour to 24 hours, preferably for about 8 hours. Resulting compounds of Formula (Ic) were isolated from the reaction mixture by standard techniques. The compounds of Formula (Ic) were then suspended in a neutral solvent, preferably acetone, and then treated with a base, preferably sodium bicarbonate, and thiophosgene. The reaction mixture was then allowed to reflux at temperatures from about 30° C. to about 120° C., for about 1 hour to about 24 hours, preferably 5 hours, to form the compounds of Formula (Id), which were isolated from the reaction mixture by standard isolation techniques.

C. Synthesis of Compounds of Formula (Ie)

The compounds of Formula (Ie) are the compounds of Formula (I) wherein Z is sulfur; $R^1$ is hydrogen; $R^2$, $R^3$, $R^4$ and $R^5$ are independently hydrogen, halo, lower alkyl, lower haloalkyl, lower alkoxy, lower haloalkoxy, nitro, cyano, phenoxy, halophenoxy, haloalkylphenoxy or thiocyano. Compounds of Formula (Ie) are synthesized from compounds of Formulae (C), (D) and (E), as shown in the following Reaction Scheme 3:

REACTION SCHEME 3

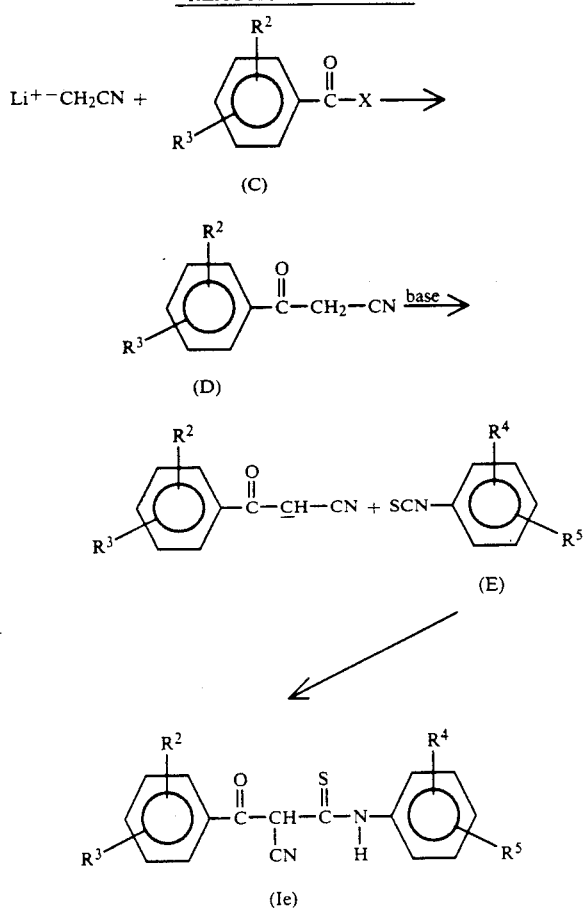

Compounds of Formulae (C) and (E) are commercially available.

In general, the compounds of Formula (Ie) are prepared by first treating acetonitrile in an ethereal solvent, preferably tetrahydrofuran, with an alkyllithium, preferably n-butyllithium, at temperatures from about −100° C. to about −20° C. and for about 15 minutes to about 4 hours, preferably for about 30 minutes, to form the anion of acetonitrile. The anion is then treated with compounds of Formula (C). Resulting compounds of Formula (D) are then isolated from the reaction mixture by standard isolation techniques. Compounds of Formula (D) are then dissolved in solvent, preferably tetrahydrofuran, and then treated with a strong base, preferably sodium hydride, to form anions of the compounds of Formula (D). These anions are then treated with phenyl isothiocyanates of Formula (E) to form compounds of Formula (Ie), which are separated from the reaction mixture by standard isolation techniques.

The following specific preparations and examples are provided as a guide to assist in the practice of the invention, and are not intended as a limitation on the scope of the invention.

PREPARATION 1

(4-cyano-2-methylaniline)

A. To a stirred suspension of 3-methyl-4-nitrobenzoic acid (50 g, 0.276 mol) in ethyl acetate (500 mL) was added thionyl chloride (100 mL) and 10 drops of dimethylformamide. The reaction mixture was stirred overnight. The solvent was then removed under reduced pressure and the resulting yellow oil was added dropwise to a stirred, 0° C. solution of tetrahydrofuran (1500 mL) saturated with $NH_3$. After stirring for 3 hours at 0° C., the solvent was removed. The resulting white solid was partitioned between ethyl acetate and $H_2O$. The organic phase was then washed with aqueous sodium bicarbonate, dried ($Na_2SO_4$) and evaporated under reduced pressure to afford 38.2 g (78%) of 3-methyl-4-nitrobenzamide, as a yellow solid; m.p. 144°–145° C.

B. To a stirred, 0° C. solution of 3-methyl-4-nitrobenzamide (30 g, 0.169 mol) in dichloromethane (900 mL) under nitrogen was added pyridine (29.5 g, 0.373 mol), then dropwise trifluoroacetic anhydride (42.7 g, 0.203 mol) in dichloromethane (90 mL). The reaction mixture was stirred at 0° C. for one hour and then 1N HCl was added. The organic phase was separated, dried ($Na_2SO_4$) and concentrated under reduced pressure to afford 25.5 g (93%) of the 3-methyl-4-nitrobenzonitrile as a light yellow solid; m.p. 69°–71° C.

C. To a stirred, 25° C. solution of 3-methyl-4-nitrobenzonitrile (24 g, 0.148 mol) in acetic acid (250 mL) under nitrogen was added dropwise a solution of $SnCl_2.2H_2O$ (133.57 g., 0.592 mol) in concentrated HCl (250 mL). After stirring for 3 hours, the reaction mixture was added carefully to excess cold ammonium hydroxide. The reaction mixture was extracted several times with ethyl ether. The organic extracts were then combined, dried ($Na_2SO_4$) and evaporated under reduced pressure to afford 12 g (61%) of the title compound, 4-cyano-2-methylaniline, as a white solid; m.p. 64°–66° C.

D. In a similar manner, but replacing 3-methyl-4-nitrobenzoic acid with other appropriately substituted benzoic acids, the following compounds are made:
3-chloro-4-cyanoaniline.

PREPARATION 2

(2-chloro-4-cyanoaniline)

To a stirred, 60° C. solution of 4-cyanoaniline (20 g, 0.169 mol) in acetonitrile (200 mL) was added slowly N-chlorosuccinimide (24.8 g, 0.186 mol) to keep the reaction at reflux. After the addition of the N-chlorosuccinimide was complete, the reaction mixture was stirred at 60° C. for two hours. The solvent was then removed under reduced pressure. The residue was then dissolved in dichloromethane, washed with a 5% sodium hydroxide solution, dried ($Na_2SO_4$) and evaporated under reduced pressure to afford 24.5 g (95%) of the title compound, 2-chloro-4-cyanoaniline, as a tan solid; m.p. 93°–95° C.

PREPARATION 3

(3-chloro-4-nitroaniline)

A. To 3-chloroaniline (10 g, 0.078 mol) was added portionwise acetic anhydride (32 g, 0.314 mol) in such a manner as to keep the temperature of the reaction mixture below 85° C. The reaction mixture was then stirred at 90° C. for 4 hours and then cooled to room temperature. The reaction mixture was then poured carefully into ice water, extracted with ethyl acetate and dried over sodium sulfate. The solvent was removed, yielding 30 g of N-acetyl-3-chloroaniline.

B. To fuming nitric acid (120 mL) at −50° C. was added N-acetyl-3-chloroaniline (30 g) over a period of 45 minutes. The reaction was kept between −50° C. and −30° C. using a dry ice/acetone bath. The reaction mixture was stirred for an additional hour and then poured into 1500 mL of crushed ice and water. The precipitate was filtered and slurried with 1 liter of slightly alkaline water (ammonium hydroxide) twice. The precipitate was then dried and recrystallized from toluene to yield (3.6 g) of N-acetyl-3-chloro-4-nitroaniline; m.p. 134°–136° C.

C. To concentrated HCl (15 mL) at reflux under nitrogen was added N-acetyl-3-chloro-4-nitroaniline (3 g, 0.014 mol). The reaction mixture was stirred for 3 hours. A white precipitate formed upon cooling to room temperature. The reaction mixture was then diluted with water, extracted with ethyl acetate and dried over sodium sulfate. The solvent was then removed under reduced pressure to afford 2.1 g (87%) of the title compound, 3-chloro-4-nitroaniline, as a yellow solid; m.p. 157°–158° C.

PREPARATION 4

(α-cyano-4-trifluoromethylacetanilide)

A. To a stirred, 0° solution of 4-trifluoromethylaniline (21.2 g; 0.135 mol) and cyanoacetic acid (18.2 g; 0.214 mol) in dimethylformamide (140 mL) was added diisopropyl carbodiimide (18.7 g; 0.148 mol) portionwise over 10 minutes. The reaction was allowed to warm to room temperature over 1 hour and then diluted with 150 mL of hexane-ethyl acetate (1:1). The reaction was filtered to remove the urea by-product, and the filtrate was partitioned between 1N aqueous HCl (500 mL) and ethyl acetate (500 mL). The aqueous phase was discarded and the organic phase washed with brine and then dried over sodium sulfate. The solvent was removed under reduced pressure to give a solid which was recrystallized in absolute ethanol to give 21.2 g (60%) of the title compound, α-cyano-4-trifluoromethylacetanilide; m.p. 191°–3° C.

B. In a similar manner, but replacing 4-trifluoromethylaniline with other appropriately substituted anilines, the following compounds are prepared:
α-cyano-4-fluoroacetanilide;
α-cyano-4-chloroacetanilide;
α-cyano-4-bromoacetanilide;
α-cyano-4-iodoacetanilide;
α-cyano-3-chloro-4-chloroacetanilide;
α-cyano-2-chloro-4-chloroacetanilide;
α-cyano-4-chloro-3-trifluoromethylacetanilide;
α-cyano-4-chloro-2-methylacetanilide;
α-cyano-4-bromo-3-methylacetanilide;
α-cyano-3-trifluoromethylacetanilide;
α-cyano-2-trifluoromethylacetanilide;
α-cyano-4-cyanoacetanilide;
α-cyano-4-methoxyacetanilide;
α-cyano-4-nitro-2-chloroacetanilide;
α-cyano-4-chloro-2-nitroacetanilide;
α-cyano-2-methyl-4-nitroacetanilide;
α-cyano-4-methyl-3-trifluoromethylacetanilide;
α-cyano-3-chloroacetanilide;
α-cyano-3-chloro-5-chloroacetanilide;
α-cyano-4-nitroacetanilide; and
α-cyano-3-nitroacetanilide.

PREPARATION 5

(Substituted 4-phenoxyacetanilides)

A. A solution of 4-hydroxyaniline (12.2 g, 0.11 mol) in dimethylsulfoxide (100 mL) was treated portionwise with sodium hydride (4.4 g of a 60% oil dispersion) under a nitrogen atmosphere. The reaction mixture was heated at 80° C. for one hour and then treated with 4-bromobenzotrifluoride (25 g., 0.11 mol). The reaction mixture was heated at 100° C. for 12 hours and then cooled to room temperature. The reaction was partitioned between ether and aqueous sodium hydroxide (1N), the organic phase dried over magnesium sulfate, filtered and then treated with excess ethereal HCl. The resulting solid was filtered off and partitioned between ether and aqueous sodium hydroxide (1N). The organic phase was dried over magnesium sulfate and concentrated to give 7.2 g of 4-(4'-trifluoromethyl)phenoxyaniline. Condensation of 4-(4'-trifluoromethyl)phenoxyaniline with cyanoacetic acid as described in Preparation 4 gave 6.3 g of α-cyano-4-(4'-trifluoromethyl)phenoxyacetanilide, m.p. 186°–188° C.

B. In a similar manner, but substituting 4-hydroxyaniline with appropriately substituted anilines, the following compounds were made:
α-cyano-2-methyl-4-(4'-trifluoromethyl)phenoxyacetanilide; and
α-cyano-2,6-dimethyl-4-(4'-trifluoromethyl)phenoxyacetanilide.

C. To a solution of 4-chlorophenol (11.4 g, 0.09 mol) in dimethylsulfoxide was added portionwise sodium hydride (3.5 g of a 60% oil suspension). When gas evolution was complete the solution was treated with 3,4-dichloronitrobenzene (15.3 g) and heated at 85° C. for 24 hours. The reaction mixture was cooled to room temperature and partitioned between ether and water. The organic phase was washed with aqueous sodium hydroxide (0.5N), hydrochloric acid (1N), dried over magnesium sulfate and concentrated to a solid. The solid was washed with ethanol to give 18.5 g of 4-(4'-chloro)phenoxy-3-chloronitrobenzene. To a suspension of 4-(4'-chloro)phenoxy-3-chloronitrobenzene (7.2 g, 0.025 mol) in 125 mL glacial acetic acid was added a solution of stannous chloride dihydrate (16 g) in 125 mL of concentrated aqueous hydrochloric acid. The reaction mixture was heated at reflux for three hours and then cooled to room temperature. The reaction mixture was then filtered and the solid washed with a small amount of cold water. The solid was then partitioned between aqueous sodium hydroxide (0.5N) and ether. The organic phase was removed and dried over magnesium sulfate to give 4-(4'-chloro)phenoxy-3-chloroaniline. Condensation of 4-(4'-chloro)phenoxy-3-chloroaniline with cyanoacetic acid as described in Preparation 4 above gave 4.0 g of α-cyano-4-(4'-chloro)phenoxy-3-chloroacetanilide, m.p. 188°–90° C.

D. In a similar manner, but substituting 4-chlorophenol with the appropriately substituted phenol, and 3,4-dichloronitrobenzene with the appropriately substituted nitrobenzene, the following compound was made:
α-cyano-4-(3'-trifluoromethyl)phenoxyacetanilide.

PREPARATION 6

(α-cyano-N-methyl-4-trifluoromethylacetanilide)

A. A mixture of 4-trifluoromethylaniline (6.7 g), trimethylorthoformate (6.6 g) and sulfuric acid (0.22 g) was heated at 90° C. and the methanol formed in the reaction was allowed to distill off. Additional trimethylorthoformate (4 mL) was added twice more. After each addition the reaction mixture was distilled. A final aliquot trimethylorthoformate (5 mL) was added and the reaction mixture was heated at 150° C. for four hours. The reaction mixture was cooled and partitioned between saturated aqueous sodium bicarbonate and ethyl acetate. The organic layer was removed, dried over sodium sulfate, and concentrated to a yellow oil. This oil was then suspended in 2N aqueous HCl (100 mL) and then heated at 80° C. for eight hours. The reaction mixture was then cooled, made basic to pH 11 with aqueous NaOH, and extracted with ether. The organic layer was dried over magnesium sulfate and concentrated to an oil. This oil was further purified by chromatography on silica gel (350 g, elute with hexane:ether (60/40)) to give 5.8 g of N-methyl-4-trifluoromethylaniline as a low-melting solid. Condensation of N-methyl-4-trifluoromethylaniline with cyanoacetic acid, as described in Preparation 1 yielded 6.0 g of α-cyano-N-methyl-4-trifluoromethylacetanilide; m.p. 68°–70° C.

B. In a similar manner, but replacing N-methyl-4-trifluoromethylaniline with N-methyl-4-chloroaniline, which was commercially available, the following compound was made:
α-cyano-N-methyl-4-chloroacetanilide.

C. In a similar manner, but replacing 4-trifluoromethylaniline with other appropriately substituted anilines, the following compound are made:
α-cyano-N-methyl-4-bromoacetanilide; and
α-cyano-N-methyl-4-trifluoromethoxyacetanilide;

PREPARATION 7

(α-cyano-4-thiocyanoacetanilide)

To a −10° C., mechanically-stirred solution of aniline (21 g) and ammonium thiocyanate (52.1 g) in methanol (230 mL) was added a solution of bromine (38.7 g) in sodium bromide-saturated methanol. The rate of addition was adjusted such that the temperature of the reaction mixture did not rise above 0° C. After the addition was complete, the reaction mixture was stirred for one hour. The reaction mixture was then poured into a mixture of water (one liter), saturated aqueous sodium bicarbonate (500 mL) and ether (500 mL). The reaction mixture was then stirred for one hour and the phases separated. The organic phase was washed with brine, dried over magnesium sulfate and concentrated to yield an oil, which solidified upon trituration with hexane. The resulting solid was filtered and washed with hexane to afford 30.5 g of 4-thiocyanoaniline. Condensation of 4-thiocyanoaniline (5.7 g) with cyanoacetic acid, as described in Preparation 1, afforded 5.1 g of the title compound, α-cyano-4-thiocyanoacetanilide; m.p. 165°–166° C.

PREPARATION 8

(4-chloro-2-methylbenzoic acids)

A. To a stirred 0° C. suspension of cuprous chloride (4.95 g, 0.050 mol) in 20 mL $H_2O$ was added sodium cyanide (6.5 g, 0.133 mol) in 25 mL $H_2O$ to form the copper cyanide solution.

B. To a stirred, 0° C. solution of 6N HCl (12 mL) was added 4-chloro-2-methyl aniline (5.7 g, 0.040 mol). Ice was added to the reaction mixture to maintain a temperature of 0° C. Sodium nitrite (2.8 g, 0.040 mol) in 8 mL $H_2O$ was then added dropwise, followed by the addition of more ice to the reaction mixture. After being tested for free nitrous acid with starch-iodide paper, the reaction mixture was carefully neutralized with solid sodium carbonate to form the diazonium salt of the aniline.

C. Toluene (30 mL) and ice was added to the above copper cyanide solution and then the reaction mixture was stirred vigorously. The above diazonium salt solution was then slowly added to the reaction mixture. After the addition was complete, the reaction mixture was stirred at 0° C. for 30 minutes. The reaction mixture was then allowed to warm to room temperature (25° C.), and then stirred for another hour. The reaction mixture was then heated to 50° C. for 2 hours without stirring. The toluene phase and precipitate were then separated from the aqueous phase. To the toluene phase was added 10 mL concentrated HCl, 40 mL hot $H_2O$, and $FeCl_3.6H_2O$ (32 g, 0.118 mol) and this reaction mixture was then stirred overnight. The reaction mixture was then added to 200 mL $H_2O$. The organic phase was then extracted with toluene, dried and evaporated under reduced pressure to produce 4-chloro-2-methylbenzonitrile as a dark brown oil.

D. To a solution of 15 mL of concentrated sulfuric acid in 18 mL $H_2O$ was added 4-chloro-2-methylbenzonitrile (7 g). The reaction mixture was heated at reflux for 18 hours. The reaction mixture was then allowed to cool to room temperature and then partitioned between ethyl acetate and $H_2O$. The aqueous layer was discarded. The remaining organic phase was extracted with aqueous potassium carbonate. The resulting aqueous phase was then washed with ethyl acetate. The aqueous phase was then carefully acidified with dilute HCl. The organic phase was then extracted with ethyl acetate, dried with sodium sulfate and evaporated under reduced pressure to give 1.04 g (18%) of the title compound, 4-chloro-2-methylbenzoic acid, as a white solid; m.p. 163°–165° C.

PREPARATION 9

(4-(4-chlorophenoxy)benzoic acid)

A. To a stirred solution of 4-fluoroacetophenone (20 g, 0.145 mol) and 4-chlorophenol (26.07 g, 0.203 mol) in N,N-dimethylacetamide (200 mL) was added potassium carbonate (26.22 g, 0.19 mol). The resulting slurry mixture was heated overnight under nitrogen at 150° C. The mixture was then allowed to cool to room temperature and then added to $H_2O$ (250 mL). The mixture was then extracted with toluene. The organic phase was then washed with dilute sodium hydroxide, dried ($Na_2SO_4$) and concentrated to afford a brown liquid. The liquid was further purified by vacuum distillation. Upon standing, a light-yellow solid formed. Further purification by trituration with hexane yielded 18.4 g (52%) of 4-(4-chlorophenoxy)acetophenone as a white solid, m.p. 60°–62° C.

B. To a stirred, 60° C. solution of 4-(4-chlorophenoxy)acetophenone (5 g., 0.02 mol) in ethanol (40 mL) was added dropwise aqueous sodium hypochlorite (5.25%, 140 mL). The mixture was stirred for 2 hours. A solution of sodium bisulfite in $H_2O$ was then added dropwise to the mixture. The mixture was then acidified with 6N HCl. The mixture was then extracted with ethyl acetate, dried ($Na_2SO_4$) and concentrated under reduced pressure to yield 4.45 g (88%) of the title compound, 4-(4-chlorophenoxy)benzoic acid, as a white crystalline solid; m.p. 161°–164° C.

C. In a similar manner, but replacing the 4-chlorophenol in Section A of this Preparation with the appropriately substituted phenol, the following compounds are prepared:
4-(4-bromophenoxy)benzoic acid;
4-(4-iodophenoxy)benzoic acid; and 4-(4-fluorophenoxy)benzoic acid.

PREPARATION 10

(Conversion of Substituted Benzoic Acids to Substituted Benzoyl Chlorides)

To a solution or suspension of the appropriately substituted benzoic acid in ethyl acetate is added 1.5 equivalents of oxalyl chloride and a trace of dimethyl formamide. The reaction mixture is stirred at room temperature for several hours until gas evolution is complete and a homogenous solution is obtained. Concentration of the solution under reduced pressure affords the corresponding benzoyl chloride.

PREPARATION 11

((4-trifluoromethyl)benzoylacetonitrile)

To a stirred, $-78°$ C. solution of acetonitrile (17.0 mL) in tetrahydrofuran (800 mL) was added over 15 minutes a 1.6M solution of n-butyllithium in hexane (150 mL). The resultant slurry was stirred at $-78°$ C. for 15 minutes and then treated over 15 minutes with 4-trifluoromethylbenzoyl chloride (12.0 mL). After 40 minutes, the reaction mixture was treated with ammonium chloride (20 g) in water (100 mL). The reaction mixture was then partitioned between aqueous 1N HCl and hexane:ethyl acetate (50/50). The organic phase was separated, washed with brine, dried over sodium sulfate and concentrated to an oil. This oil was then redissolved in ether and treated with concentrated aqueous ammonia to give a white precipitate. This precipitate was filtered off and partitioned between 1N aqueous HCl and ethyl acetate. The organic phase was then separated, dried over sodium sulfate and concentrated to an oil, which, upon trituration with warm hexane, afforded 11.4 g of the title compound, (4-trifluoromethyl)benzoylacetonitrile, as an off-white solid; m.p. 46°–47° C.

EXAMPLE 1

(α-cyano-β-oxo-N-(4'-trifluoromethylphenyl)-(4-trifluoromethyl)benzenepropanamide)

A. To a mechanically-stirred, 0° C. solution of α-cyano-4-trifluoromethylacetanilide, as prepared in Preparation 4, (21.75 g, 0.095 mol) in 450 mL tetrahydrofuran (THF) was added portionwise 8.8 g (0.22 mol) of a 60% oil dispersion of sodium hydride. The mixture was stirred for 15 minutes and then a solution of 4-(trifluoromethyl)benzoyl chloride (20.9 g, 0.10 mol) in dichloromethane (50 mL) was added dropwise over 30 minutes. After the addition was complete the reaction was stirred at 0° C. for an additional 30 minutes and then cautiously treated with 1 liter of 0.5N aqueous HCl. The solid that formed was filtered off, washed with water, ethanol and dried under vacuum. Recrystallization of this material from toluene gave 30 g of the title compound, α-cyano-β-oxo-N-(4'-trifluoromethyl)phenyl-(4-trifluoromethyl)benzenepropanamide; m.p. 221°–3° C.

B. In a similar manner, but replacing α-cyano-4-trifluoromethylacetanilide with other appropriately substituted acetanilides, and replacing 4-(trifluoromethyl)benzoyl chloride with other appropriately substituted benzoyl chlorides, the following compounds were made:

α-cyano-β-oxo-N-(4'-trifluoromethyl)phenyl-(4-fluoro)benzenepropanamide, m.p. 211°–3° C.;
α-cyano-β-oxo-N-(4'-trifluoromethyl)phenyl-(4-chloro)benzenepropanamide, m.p. 218°–20° C.;
α-cyano-β-oxo-N-(4'-trifluoromethyl)phenyl-(4-bromo)benzenepropanamide, m.p. 213°–4° C.;
α-cyano-β-oxo-N-(4'-trifluoromethyl)phenyl-(4-iodo)benzenepropanamide, m.p. 239°–40° C.;
α-cyano-β-oxo-N-(4'-trifluoromethyl)phenyl-(4-trifluoromethoxy)benzenepropanamide, m.p. 188°–90° C.;
α-cyano-β-oxo-N-(4'-trifluoromethyl)phenyl-(2-trifluoromethyl)benzenepropanamide, m.p. 151°–3° C.;
α-cyano-β-oxo-N-(4'-trifluoromethyl)phenyl-(3-trifluoromethyl)benzenepropanamide, m.p. 165°–6° C.;
α-cyano-β-oxo-N-(4'-trifluoromethyl)phenyl-(3-chloro)benzenepropanamide, m.p. 201°–2° C.;
α-cyano-β-oxo-N-(4'-trifluoromethyl)phenyl-(2-chloro-4-chloro)benzenepropanamide, m.p. 187°–8° C.;
α-cyano-β-oxo-N-(4'-trifluoromethyl)phenyl-(3-chloro-4-chloro)benzenepropanamide, m.p. 187°–8° C.;
α-cyano-β-oxo-N-(4'-trifluoromethyl)phenyl-(3-chloro-5-chloro)benzenepropanamide, m.p. 208°–10° C.;
α-cyano-β-oxo-N-(4'-trifluoromethyl)phenyl-(4-methyl)benzenepropanamide, m.p. 259°–61° C.;
α-cyano-β-oxo-N-(4'-trifluoromethyl)phenyl-(4-methoxy)benzenepropanamide, m.p. 248°–9° C.;
α-cyano-β-oxo-N-(4'-trifluoromethyl)phenyl-(4-nitro)benzenepropanamide, m.p. 211°–4° C.;
α-cyano-β-oxo-N-(4'-trifluoromethyl)phenyl-(3-nitro)benzenepropanamide, m.p. 192°–4° C.;
α-cyano-β-oxo-N-(4'-trifluoromethyl)phenyl-(4-cyano)benzenepropanamide, m.p. 252°–4° C.;
α-cyano-β-oxo-N-(4'-trifluoromethyl)phenyl-(4-chloro-2-methyl)benzenepropanamide, m.p. 189°–91° C.;
α-cyano-β-oxo-N-(4'-trifluoromethyl)phenyl-(4-(4-chlorophenoxy))benzenepropanamide, m.p. 233°–5° C.;
α-cyano-β-oxo-N-(4'-trifluoromethyl)phenyl-(4-(4-bromophenoxy))benzenepropanamide, m.p. 239°–40° C.;
α-cyano-β-oxo-N-(4'-fluoro)phenyl-(4-chloro)benzenepropanamide, m.p. 232°–3° C.;
α-cyano-β-oxo-N-(4'-fluoro)phenyl-(4-bromo)benzenepropanamide, m.p. 208°–10° C.;
α-cyano-β-oxo-N-(4'-fluoro)phenyl-(4-iodo)benzenepropanamide, m.p. 213°–5° C.;
α-cyano-β-oxo-N-(4'-fluoro)phenyl-(4-trifluoromethyl)benzenepropanamide, m.p. 196°–8° C.;
α-cyano-β-oxo-N-(4'-chloro)phenyl-(4-fluoro)benzenepropanamide, m.p. 243°–5° C.;
α-cyano-β-oxo-N-(4'-chloro)phenyl-(4-chloro)benzenepropanamide, m.p. 225°–6° C.;
α-cyano-β-oxo-N-(4'-chloro)phenyl-(4-bromo)benzenepropanamide, m.p. 234°–5° C.;
α-cyano-β-oxo-N-(4'-chloro)phenyl-(4-iodo)benzenepropanamide, m.p. 238°–9° C.;
α-cyano-β-oxo-N-(4'-chloro)phenyl-(3-chloro)benzenepropanamide, m.p. 218°–20° C.;
α-cyano-β-oxo-N-(4'-chloro)phenyl-(4-trifluoromethyl)benzenepropanamide, m.p. 221°–2° C.;
α-cyano-β-oxo-N-(4'-chloro)phenyl-(3-chloro-4-chloro)benzenepropanamide, m.p. 235°–7° C.;
α-cyano-β-oxo-N-(4'-chloro)phenyl-(4-(4-chlorophenoxy))benzenepropanamide, m.p. 230°–2° C.;
α-cyano-β-oxo-N-(4'-bromo)phenyl-(4-fluoro)benzenepropanamide, m.p. 231°–3° C.;
α-cyano-β-oxo-N-(4'-bromo)phenyl-(4-chloro)benzenepropanamide, m.p. 243°–4° C.;

α-cyano-β-oxo-N-(4'-bromo)phenyl-(4-bromo)benzenepropanamide, m.p. 251°-3° C.;
α-cyano-β-oxo-N-(4'-bromo)phenyl-(4-iodo)benzenepropanamide, m.p. 258°-9° C.;
α-cyano-β-oxo-N-(4'-bromo)phenyl-(4-trifluoromethyl)benzenepropanamide, m.p. 237°-8° C.;
α-cyano-β-oxo-N-(4'-chloro)phenyl-(4-(4-bromophenoxy))benzenepropanamide, m.p. 235°-7° C.;
α-cyano-β-oxo-N-(4'-iodo)phenyl-(4-trifluoromethyl)benzenepropanamide, m.p. 256°-8° C.;
α-cyano-β-oxo-N-(4'-iodo)phenyl-(4-iodo)benzenepropanamide, m.p. 278°-9° C.;
α-cyano-β-oxo-N-(4'-trifluoromethoxy)phenyl-(4-trifluoromethyl)benzenepropanamide, m.p. 209°-10° C.;
α-cyano-β-oxo-N-(4'-trifluoromethoxy)phenyl-(4-trifluoromethoxy)benzenepropanamide, m.p. 198°-200° C.;
α-cyano-β-oxo-N-(3'-chloro-4'-chloro)phenyl-(4-chloro)benzenepropanamide, m.p. 234°-6° C.;
α-cyano-β-oxo-N-(3'-chloro-4'-chloro)phenyl-(4-trifluoromethyl)benzenepropanamide, m.p. 187°-8° C.;
α-cyano-β-oxo-N-(3'-chloro-4'-chloro)phenyl-(3-chloro-4-chloro)benzenepropanamide, m.p. 229°-30° C.;
α-cyano-β-oxo-N-(2'-chloro-4'-chloro)phenyl-(4-trifluoromethyl)benzenepropanamide, m.p. 148°-50° C.;
α-cyano-β-oxo-N-(3'-trifluoromethyl)benzenepropanamide, m.p. 172°-3° C.;
α-cyano-β-oxo-N-(4'-chloro-3'-trifluoromethyl)phenyl-(4-chloro)-benzenepropanamide, m.p. 189°-91° C.;
α-cyano-β-oxo-N-(4'-chloro-2'-methyl)phenyl-(4-iodo)-benzenepropanamide, m.p. 171°-3° C.;
α-cyano-β-oxo-N-(4'-chloro-2'-methyl)phenyl-(4-chloro)benzenepropanamide, m.p. 181°-3° C.;
α-cyano-β-oxo-N-(4'-chloro-2'-methyl)phenyl-(4-bromo)benzenepropanamide, m.p. 170°-2° C.;
α-cyano-β-oxo-N-(4'-chloro-2'-methyl)phenyl-(4-iodo)-benzenepropanamide, m.p. 186°-7° C.;
α-cyano-β-oxo-N-(4'-chloro-2'-methyl)phenyl-(4-trifluoromethyl)benzenepropanamide, m.p. 150°-2° C.;
α-cyano-β-oxo-N-(4'-chloro-2'-methyl)phenyl-(4-chloro-2-methyl)benzenepropanamide, m.p. 162°-4° C.;
α-cyano-β-oxo-N-(4'-bromo-3'-methyl)phenyl-(4-trifluoromethyl)benzenepropanamide, m.p. 185°-7° C.;
α-cyano-β-oxo-N-(3'-trifluoromethyl-5'-trifluoromethyl)phenyl-(4-trifluoromethyl)-benzenepropanamide, m.p. 190°-2° C.;
α-cyano-β-oxo-N-(3'-trifluoromethyl)phenyl-(4-trifluoromethyl)benzenepropanamide, m.p. 138°-40° C.;
α-cyano-β-oxo-N-(3'-trifluoromethyl)phenyl-(4-bromo)benzenepropanamide, m.p. 162°-5° C.;
α-cyano-β-oxo-N-(2'-trifluoromethyl)phenyl-(4-trifluoromethyl)benzenepropanamide, m.p. 122°-4° C.;
α-cyano-β-oxo-N-(2'-trifluoromethyl)phenyl-(4-chloro)benzenepropanamide, m.p. 125°-6° C.;
α-cyano-β-oxo-N-(4'-cyano)phenyl-(4-bromo)benzenepropanamide, m.p. 242°-4° C.;
α-cyano-β-oxo-N-(4'-cyano)phenyl-(4-trifluoromethyl)benzenepropanamide, m.p. 206°-8° C.;
α-cyano-β-oxo-N-(4'-cyano)phenyl-(4-cyano)benzenepropanamide, m.p. 260°-2° C.;
α-cyano-β-oxo-N-(4'-trifluoromethoxy)phenyl-(4-trifluoromethyl)benzenepropanamide, m.p. 248°-50° C.;
α-cyano-β-oxo-N-(4'-cyano-2'-methyl)phenyl-(4-trifluoromethyl)benzenepropanamide, m.p. 216°-8° C.;
α-cyano-β-oxo-N-(4'-cyano-2'-methyl)phenyl-(4-chloro)benzenepropanamide, m.p. 244°-5° C.;
α-cyano-β-oxo-N-(3'-chloro-4'-cyano)phenyl-(4-trifluoromethyl)benzenepropanamide, m.p. 196°-7° C.;
α-cyano-β-oxo-N-(3'-chloro-4'-cyano)phenyl-(4-chloro)benzenepropanamide, m.p. 262°-3° C.;
α-cyano-β-oxo-N-(3'-chloro-4'-cyano)phenyl-(3-chloro)benzenepropanamide, m.p. 243°-4° C.;
α-cyano-β-oxo-N-(2'-chloro-4'-cyano)phenyl-(4-trifluoromethyl)benzenepropanamide, m.p. 205°-7° C.;
α-cyano-β-oxo-N-(4'-nitro)phenyl-(4-trifluoromethyl)benzenepropanamide, m.p. 245°-7° C.;
α-cyano-β-oxo-N-(4'-nitro)phenyl-(3-trifluoromethyl)benzenepropanamide, m.p. 207°-8° C.;
α-cyano-β-oxo-N-(2'-chloro-4'-nitro)phenyl-(4-trifluoromethyl)benzenepropanamide, m.p. 167°-8° C.;
α-cyano-β-oxo-N-(2'-nitro-4'-chloro)phenyl-(4-trifluoromethyl)benzenepropanamide, m.p. 170°-2° C.;
α-cyano-β-oxo-N-(2'-nitro-4'-chloro)phenyl-(4-chloro)-benzenepropanamide, m.p. 193°-4° C.;
α-cyano-β-oxo-N-(2'-methyl-4'-nitro)phenyl-(4-trifluoromethyl)benzenepropanamide, m.p. 190°-1° C.;
α-cyano-β-oxo-N-(4'-nitro-3'-trifluoromethyl)phenyl-(4-trifluoromethyl)benzenepropanamide, m.p. 195°-7° C.;
α-cyano-β-oxo-N-(4'-nitro-3'-trifluoromethyl)phenyl-(4-chloro)benzenepropanamide, m.p. 199°-201° C.;
α-cyano-β-oxo-N-(2'-nitro-4'-trifluoromethyl)phenyl-(4-chloro)benzenepropanamide, m.p. 170°-1° C.;
α-cyano-β-oxo-N-(2'-nitro-4'-trifluoromethyl)phenyl-(4-trifluoromethyl)benzenepropanamide, m.p. 196°-8° C.;
α-cyano-β-oxo-N-(3'-chloro-4'-nitro)phenyl-(4-chloro)benzenepropanamide, m.p. 211°-12° C.;
α-cyano-β-oxo-N-(3'-chloro-4'-nitro)phenyl-(4-bromo)benzenepropanamide, m.p. 213°-15° C.;
α-cyano-β-oxo-N-(3'-chloro-4'-nitro)phenyl-(4-trifluoromethyl)benzenepropanamide, m.p. 185°-7° C.;
α-cyano-β-oxo-N-(4'-chloro-3'-nitro)phenyl-(4-chloro)benzenepropanamide, m.p. 203°-4° C.;
α-cyano-β-oxo-N-(3'-nitro-4'-trifluoromethyl)phenyl-(4-trifluoromethyl)benzenepropanamide, m.p. 203°-5° C.;
α-cyano-β-oxo-N-(3'-nitro-4'-trifluoromethyl)phenyl-(4-cyano)benzenepropanamide, m.p. 223°-5° C.;
α-cyano-β-oxo-N-(4'-nitro)phenyl-(3-chloro)benzenepropanamide, m.p. 245°-7° C.;
α-cyano-β-oxo-N-(4'-(4-trifluoromethyl)phenoxy-2'-methyl)phenyl-(4-trifluoromethyl)benzenepropanamide, m.p. 140°-1° C.;
α-cyano-β-oxo-N-(4'-(4-trifluoromethyl)phenoxy)phenyl-(4-trifluoromethyl)benzenepropanamide, m.p. 170°-1° C.;
α-cyano-β-oxo-N-(3'-chloro-4'-(4-chlorophenoxy))phenyl-(4-trifluoromethyl)benzenepropanamide, m.p. 210°-11° C.;
α-cyano-β-oxo-N-(4'-thiocyano)phenyl-(4-trifluoromethyl)benzenepropanamide, m.p. 199°-200° C.;
α-cyano-β-oxo-N-(3'-chloro-4'-(4-chlorophenoxy))phenyl-(4-fluoro)benzenepropanamide, m.p. 168°-9° C.; and
α-cyano-β-oxo-N-(2'-methyl-4'-(4-trifluoromethylphenoxy))phenyl-(4-fluoro)benzenepropanamide, m.p. 129°-30° C.

C. In a similar manner, but replacing α-cyano-4-trifluoromethylacetanilide with the appropriately substituted N-methylacetanilide, as prepared in Sections A and B of Preparation 6 above, the following compounds were made:

α-cyano-β-oxo-N-methyl-N-(4'-trifluoromethyl)phenyl-(4-trifluoromethyl)benzenepropanamide, m.p. 118°-19° C.; and α-cyano-β-oxo-N-methyl-N-(4'-chloro)phenyl-(4-trifluoromethyl)benzenepropanamide, m.p. 155°-56° C.

D. In a similar manner, but replacing α-cyano-4-trifluoromethylacetanilide with other appropriately substituted N-methylacetanilides, as prepared in Preparation 6 above, and replacing 4-(trifluoromethyl)benzoyl chloride with other appropriately substituted benzoyl chlorides, the following compounds are made:

α-cyano-β-oxo-N-methyl-N-(4'-trifluoromethyl)phenyl-(4-chloro)benzenepropanamide;

α-cyano-β-oxo-N-methyl-N-(4'-trifluoromethoxy)phenyl-(4-chloro)benzenepropanamide;

α-cyano-β-oxo-N-methyl-N-(4'-chloro)phenyl-(4-chloro)benzenepropanamide; and

α-cyano-β-oxo-N-methyl-N-(4'-trifluoromethyl)phenyl-(4-cyano)benzenepropanamide.

EXAMPLE 2

(α-cyano-N-(4'-isothiocyano)phenyl-β-oxo-(4-trifluoromethyl)benzenepropanamide)

A suspension of α-cyano-N-(4-nitro)phenyl-β-oxo-(4-trifluoromethyl)benzenepropanamide, as prepared in Section B of Example 1, (7.33 g, 19.4 mmol) in glacial acetic acid (40 mL) was treated with a solution of $SnCl_2.2H_2O$ (15 g, 66.5 mmol) in concentrated aqueous HCL (45 mL). The reaction mixture was heated at 80° C. for 8 hours and then allowed to cool to room temperature. The reaction mixture was then poured into a mixture of water (one liter) and ethyl acetate (100 mL) and shaken in a separating funnel. The solid was filtered off, washed with water (2×100 mL) and ether (2×100 mL) and dried under reduced pressure to give 6.94 g of α-cyano-N-(4'-amino)phenyl-β-oxo-(4-trifluoromethyl)benzenepropanamide hydrochloride as a tan solid. To a suspension of α-cyano-N-(4'-amino)phenyl-β-oxo-(4-trifluoromethyl)benzenepropanamide hydrochloride (1.33 g, 3.46 mmol) in acetone (40 mL) was added sodium bicarbonate (0.87 g) and thiophosgene (0.5 g). The reaction mixture was refluxed for 5 hours, allowed to cool and then partitioned between 0.5N aqueous HCl (200 mL) and ethyl acetate (300 mL). The organic layer was washed with brine, dried over sodium sulfate and the solvent evaporated to afford a yellow solid. Recrystallization of the solid from ethyl acetate afforded 0.85 g of the title compound, α-cyano-N-(4'-isothiocyano)phenyl-β-oxo-(4-trifluoromethyl)benzenepropanamide; m.p. 230°-231° C.

EXAMPLE 3

(α-cyano-β-oxo-N-(4'-trifluoromethyl)phenyl-(4-trifluoromethyl)benzenepropanethioamide)

To a stirred, 0° C. solution of (4-trifluoromethyl)benzoylacetonitrile (0.5 g), as prepared in Preparation 11, in tetrahydrofuran (20 mL) was added sodium hydride (0.10 g of a 60% oil dispersion). After 20 minutes 4-(trifluoromethyl)phenyl isothiocyanate (0.48 g) was added and the reaction mixture stirred for another 2 hours. The solution was then partitioned between aqueous 1N HCl and ethyl acetate. The organic phase was then separated, washed with brine, dried over sodium sulfate and concentrated to a solid. Recrystallization from toluene yielded 0.40 g of the title compound, α-cyano-β-oxo-N-(4'-trifluoromethyl)phenyl-(4-trifluoromethyl)benzenepropanthioamide, as a yellow solid; m.p. 208°-210° C.

EXAMPLE 4

(In Vitro Anthelmintic Activity)

Adult *Caenorhabditis elegans* (*C. elegans*) nematodes that were grown on seeded agar plates for 4 to 6 days were taken up into a test tube with small amount of buffer (6.0 g $Na_2HPO_4$, 3.0 g $KH_2PO_4$, 5.0 g NaCl and 0.25 g $MgSO_4.7H_2O$ per liter). After the nematodes settled, the top portion of the aliquot was gently removed and the nematodes were rinsed with fresh buffer. This process was repeated once or twice until the washing was clear. The final sediment was resuspended in small amount of buffer so that each drop (~50 μL) from a transfer pipette delivered 25–50 adult nematodes.

Compounds of Formula (I) were dissolved in dimethyl sulfoxide at 10 mg/mL to give sample stock solutions. During assay, 1 mL buffer was placed in each of the 24 wells in a tissue culture plate. 10 μL of sample stock solution was added respectively to 23 of the wells. The remaining well served as a drug-free control.

One drop (~50 μL) of the nematode suspension is dropped into each well (time: 0 minutes). At time: 1 hour the number of inactive nematodes versus total in each well was recorded. Some of the results are illustrated in the following Table 1:

TABLE 1

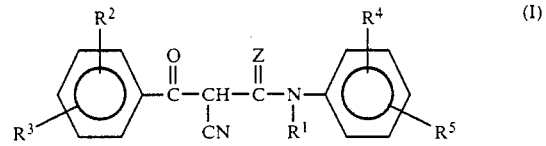

(I)

| | Z | $R^1$ | $R^2$ | $R^3$ | $R^4$ | $R^5$ | C. ELEGANS % ACTIVE |
|---|---|---|---|---|---|---|---|
| 1. | O | H | H | 4-$CF_3$ | H | 4'-$CF_3$ | 0.0 |
| 2. | O | H | H | 4-Cl | H | 4'-$CF_3$ | 0.0 |
| 3. | O | H | H | 4-I | H | 4'-$CF_3$ | 0.0 |
| 4. | O | H | 3-Cl | 4-Cl | H | 4'-$CF_3$ | 0.0 |
| 5. | O | H | H | 4-I | H | 4'-Cl | 0.0 |
| 6. | O | H | 3-Cl | 4-Cl | H | 4'-Cl | 0.0 |
| 7. | O | H | H | 4-$CF_3$ | H | 4'-I | 0.0 |
| 8. | O | H | H | 4-I | H | 4'-I | 0.0 |
| 9. | O | H | H | 4-$OCF_3$ | H | 4'-$OCF_3$ | 0.0 |
| 10. | O | H | H | 4-Cl | 3'-Cl | 4'-Cl | 0.0 |
| 11. | O | H | 3-Cl | 4-Cl | 3'-Cl | 4'-Cl | 0.0 |
| 12. | O | H | H | 4-Cl | 3'-$CF_3$ | 4'-Cl | 0.0 |
| 13. | O | H | H | 4-$CF_3$ | 3'-Cl | 4'-CN | 0.0 |
| 14. | O | H | H | 4-Cl | 3'-Cl | 4'-CN | 0.0 |
| 15. | O | H | H | 4-$CF_3$ | H | 4'-$NO_2$ | 0.0 |
| 16. | O | H | H | 4-$CF_3$ | 2'-Cl | 4'-$NO_2$ | 0.0 |
| 17. | O | H | H | 4-$CF_3$ | 3'-$CF_3$ | 4'-$NO_2$ | 0.0 |
| 18. | S | H | H | 4-$CF_3$ | H | 4'-$CF_3$ | 0.0 |

EXAMPLE 5

(In Vivo Anthelmintic Activity)

Third stage larvae of the nematode, *Nematospiroides dubius* (*N. dubius*), were collected from feces of infected mice and suspended in sterile water to a concentration of 140–160 larvae per mL of water. Eggs of the tapeworm, *Hymenolepsis nana* (*H. nana*), were collected from the intestines of infected mice and suspended in sterile water to a concentration of 4000 eggs per mL of water. Equal volumes of the *N. dubius* suspension and the *H. nana* suspension were added together to form a mixed helminth inoculum containing about 70 to 80 *N. dubius* larvae and 2000 *H. nana* eggs per mL of water.

Male Swiss-Webster mice, 18–20 gms, were challenged orally with 0.5 mL of the inoculum. Starting at 24 hours after infection, the mice were treated for eighteen (18) days ad lib with compounds of Formula (I) mixed in their food at the concentration shown in the following Table 2. Each treatment group for each compound had 4 mice. Mice were sacrificed on day nineteen (19) to examine parasite burden in the intestine. Some of the results are illustrated in the following Table 2:

TABLE 2

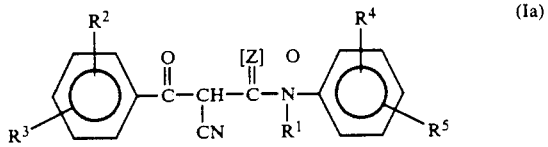

(I)

| | Z | $R^1$ | $R^2$ | $R^3$ | $R^4$ | $R^5$ | CONC. (ppm) | PERCENT REDUCTION OF PARASITES: *N. dubius*/*H. Nana* | |
|---|---|---|---|---|---|---|---|---|---|
| 1. | O | H | H | 4-OCF$_3$ | H | 4'-CF$_3$ | 125 | 100 | 100 |
| 2. | O | H | 3-CF$_3$ | H | H | 4'-CF$_3$ | 125 | 89 | 100 |
| 3. | O | H | 3-Cl | 5-Cl | H | 4'-CF$_3$ | 125 | 100 | 100 |
| 4. | O | H | H | 4-CF$_3$ | H | 4'-Cl | 62 | 65 | 78 |
| 5. | O | H | H | 4-CF$_3$ | H | 4'-Br | 125 | 100 | 95 |
| 6. | O | H | H | 4-CF$_3$ | 3'-Cl | 4'-Cl | 125 | 100 | 93 |
| 7. | O | H | H | 4-CF$_3$ | 2'-Cl | 4'-Cl | 125 | 89 | 100 |
| 8. | O | H | H | 4-CF$_3$ | H | 4'-CN | 125 | 92–100 | 74–100 |
| 9. | O | H | H | 4-CF$_3$ | 2'-CH$_3$ | 4'-CN | 125 | 90 | 100 |
| 10. | O | H | H | 4-Cl | 3'-Cl | 4'-CN | 125 | 75 | 100 |
| 11. | O | H | H | 4-CF$_3$ | 2'-Cl | 4-CN | 125 | 100 | 100 |
| 12. | O | H | H | 4-CF$_3$ | 2'-Cl | 4'-NO$_2$ | 125 | 79 | 83 |
| 13. | O | H | H | 4-CF$_3$ | 2'-CH$_3$ | 4'-NO$_2$ | 125 | 97 | 99 |
| 14. | S | H | H | 4-CF$_3$ | H | 4'-CF$_3$ | 250 | 100 | 90 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the Formula (Ia):

(Ia)

wherein
$R^1$ is hydrogen or lower alkyl; and
$R^2$, $R^3$, $R^4$ and $R^5$ are independently hydrogen, halo, lower haloalkyl, lower alkoxy, lower haloalkoxy, nitro, cyano, halophenoxy, haloalkylphenoxy or thiocyano, provided that $R^2$ and $R^3$ are not simultaneously hydrogen and that $R^4$ and $R^5$ are not simultaneously hydrogen; or a pharmaceutically acceptable salt thereof.

2. A compound of claim 1 wherein $R^5$ is in the 4'-position.

3. A compound of claim 2 wherein $R^5$ is halo, lower haloalkyl, lower haloalkoxy, nitro, cyano, halophenoxy, haloalkylphenoxy or isothiocyano.

4. A compound of claim 3 wherein $R^5$ is halo, lower haloalkyl or lower haloalkoxy.

5. A compound of claim 4 wherein $R^5$ is haloalkyl.

6. A compound of claim 5 wherein $R^2$ and $R^3$ are halo.

7. The compound of claim 6 wherein $R^1$ and $R^4$ are hydrogen, $R^2$ is chloro in the 3-position, $R^3$ is chloro in the 5-position and $R^5$ is trifluoromethyl, namely α-cyano-β-oxo-N-(4'-trifluoromethyl)phenyl-(3,5-dichloro)benzenepropanamide.

8. A compound of claim 1 wherein $R^3$ is in the 4-position.

9. A compound of claim 8 wherein $R^3$ is halo, lower haloalkyl, lower haloalkoxy, nitro, cyano or halophenoxy.

10. A compound of claim 9 wherein $R^3$ is halo, lower haloalkyl or lower haloalkoxy.

11. A compound of claim 10 wherein $R^3$ is haloalkyl.

12. A compound of claim 1 wherein $R^3$ is in the 4-position and $R^5$ is in the 4'-position.

13. A compound of claim 12 wherein $R^3$ and $R^5$ are independently halo, lower haloalkyl, lower haloalkoxy, nitro, cyano, halophenoxy, haloalkylphenoxy or isothiocyano.

14. A compound of claim 13 wherein $R^3$ and $R^5$ are independently halo, lower haloalkyl, lower haloalkoxy, cyano or nitro.

15. A compound of claim 14 wherein $R^1$, $R^2$ and $R^4$ are hydrogen and $R^3$ and $R^5$ are haloalkyl.

16. The compound of claim 15 wherein $R^3$ and $R^5$ are trifluoromethyl, namely, α-cyano-β-oxo-N-(4'-trifluoromethyl)phenyl-(4-trifluoromethyl)benzenepropanamide.

17. A compound of claim 14 wherein $R^1$, $R^2$ and $R^4$ are hydrogen, $R^3$ is halo and $R^5$ is haloalkyl.

18. The compound of claim 17 wherein $R^3$ is chloro and $R^5$ is trifluoromethyl, namely, α-cyano-β-oxo-N-(4'-trifluoromethyl)phenyl-(4-chloro)benzenepropanamide.

19. A compound of claim 14 wherein $R^1$, $R^2$ and $R^4$ are hydrogen, and $R^3$ and $R^5$ are halo.

20. The compound of claim 19 wherein $R^3$ and $R^5$ are chloro, namely, α-cyano-β-oxo-N-(4'-chloro)phenyl-(4-chloro)benzenepropanamide.

21. A compound of claim 12 wherein $R^1$ is lower alkyl.

22. A compound of claim 21 wherein $R^2$ and $R^4$ are hydrogen and $R^3$ and $R^5$ are haloalkyl.

23. A compound of claim 12 wherein $R^2$, $R^3$, $R^4$ and $R^5$ are independently halo or hydrogen.

24. A compound of claim 23 wherein $R^2$ is halo in the 3-position and $R^4$ is halo in the 3'-position.

25. The compound of claim 24 wherein $R^2$, $R^3$, $R^4$ and $R^5$ are chloro, namely, α-cyano-β-oxo-N-(3',4'-dichloro)phenyl-(3,4-dichloro)benzenepropanamide.

26. A compound of claim 23 wherein $R^2$ is halo in the 3-position and $R^4$ is hydrogen.

27. The compound of claim 26 wherein $R^2$, $R^3$ and $R^5$ are chloro, namely, α-cyano-β-oxo-N-(4'-chloro)phenyl-(3,4-dichloro)benzenepropanamide.

28. A compound of claim 23 wherein $R^4$ is halo in the 3'-position and $R^2$ is hydrogen.

29. The compound of claim 28 wherein $R^3$, $R^4$ and $R^5$ are chloro, namely, α-cyano-β-oxo-N-(3',4'-dichloro)phenyl-(4-chloro)benzenepropanamide.

30. A method for treating helminthiasis in an animal which method comprises administering to an animal in need thereof an anthelmintically effective amount of a compound of Formula (Ia):

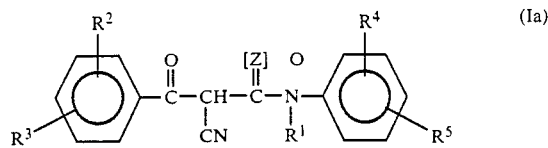

wherein
$R^1$ is hydrogen or lower alkyl; and
$R^2$, $R^3$, $R^4$ and $R^5$ are independently hydrogen, halo, lower haloalkyl, lower alkoxy, lower haloalkoxy, nitro, cyano, halophenoxy, haloalkylphenoxy or thiocyano, provided that $R^2$ and $R^3$ are not simultaneously hydrogen and that $R^4$ and $R^5$ are not simultaneously hydrogen; or a pharmaceutically acceptable salt thereof.

31. A composition for treating helminthiasis in an animal which composition comprises a pharmaceutically acceptable excipient and an anthelmintically effective amount of a compound of Formula (Ia):

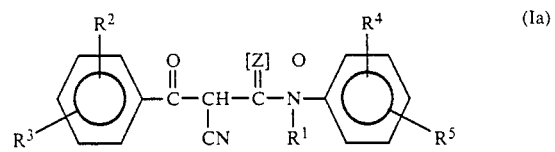

wherein
$R^1$ is hydrogen or lower alkyl; and
$R^2$, $R^3$, $R^4$ and $R^5$ are independently hydrogen, halo, lower haloalkyl, lower alkoxy, lower haloalkoxy, nitro, cyano, halophenoxy, haloalkylphenoxy or thiocyano, provided that $R^2$ and $R^3$ are not simultaneously hydrogen and that $R^4$ and $R^5$ are not simultaneously hydrogen; or a pharmaceutically acceptable salt thereof.

* * * * *